US006995575B2

(12) United States Patent
Gifford

(10) Patent No.: US 6,995,575 B2
(45) Date of Patent: Feb. 7, 2006

(54) APPARATUS AND METHODS FOR MEASURING RESISTANCE OF CONDUCTIVE LAYERS

(75) Inventor: Carl B. Gifford, Buckley, WA (US)

(73) Assignee: The Boeing Company, Chicago, IL (US)

(*) Notice: Subject to any disclaimer, the term of this patent is extended or adjusted under 35 U.S.C. 154(b) by 0 days.

(21) Appl. No.: 10/427,359

(22) Filed: Apr. 30, 2003

(65) Prior Publication Data
US 2004/0217762 A1 Nov. 4, 2004

(51) Int. Cl.
G01R 27/08 (2006.01)
(52) U.S. Cl. ............................. 324/691; 324/724
(58) Field of Classification Search ............ 324/600, 324/691, 693, 696, 700, 718, 724, 754
See application file for complete search history.

(56) References Cited

U.S. PATENT DOCUMENTS

| | | | |
|---|---|---|---|
| 3,783,375 A * | 1/1974 | Bennett | 324/601 |
| 3,936,736 A | 2/1976 | Ray | |
| 4,570,116 A | 2/1986 | Tedd et al. | |
| 4,831,876 A | 5/1989 | Porth et al. | |
| 5,228,776 A | 7/1993 | Smith et al. | |
| 5,978,074 A | 11/1999 | Opsal et al. | |
| 6,054,868 A | 4/2000 | Borden et al. | |
| 6,218,848 B1 * | 4/2001 | Hembree et al. | 324/754 |
| 6,313,647 B1 | 11/2001 | Feng et al. | |

OTHER PUBLICATIONS

Nelson, Rick, High Speeds and Fine Precision Knock PCB Traces Off Pedestal, Test & Measurement World, Jan. 1, 2000, pp. 1-5, Newton, MA, USA.

* cited by examiner

Primary Examiner—Walter Benson
(74) Attorney, Agent, or Firm—Black Lowe & Graham, PLLC

(57) ABSTRACT

Apparatus and methods of measuring the electrical resistance of electrically-conductive materials are disclosed. In one aspect, an apparatus includes a substrate, and first, second, third, and fourth elongated conductive members. Each conductive member includes a first portion at least partially disposed on the substrate and a second portion. Each of the first portions is spaced apart from one or more adjacent first portions and is engageable with the electrically-conductive material along a contact length. The apparatus may include a source operatively coupled to the second portions of the first and fourth conductive members, and a meter operatively coupled to the second portions of second and third conductive members.

24 Claims, 4 Drawing Sheets

APPARATUS AND METHODS FOR MEASURING RESISTANCE OF CONDUCTIVE LAYERS

CROSS REFERENCE TO RELATED APPLICATIONS

This patent application is related to a concurrently-filed patent application entitled "Apparatus and Methods for Measuring, Resistance of Conductive Layers" and bearing attorney docket number BOEI-1-1173, which application is hereby incorporated by reference.

FIELD OF THE INVENTION

The present disclosure relates to measuring electrical resistance and, more specifically, to measuring electrical resistance of layers of conductive material.

BACKGROUND OF THE INVENTION

Due to continuing improvements in materials technology, modern aerospace vehicles include an increasing amount of structural components made of composite materials. Because vehicle components made of non-conducting composite materials may become degraded when subjected to an electrical discharge (e.g. a lightning strike), such components are typically coated with an electrically conductive material, such as conductive paints, anti-static coatings, and the like.

Throughout various stages of development of such aerospace vehicles, measurements are often made of electrical resistance of a conductive layer that is disposed on a composite component of the vehicle. One known test device that has been successfully used for this purpose is shown in FIG. 1. As shown in FIG. 1, the prior art test device 100 includes first and second conductive strips 102, 104 disposed on a non-conductive layer 106 that is attached to a non-conductive substrate 110. In this example, the substrate 110 includes a flexible, compliant layer 111. Each conductive strip 102, 104 is operatively coupled to a conductive lead 112, 114 that extends from the test device 100 to a suitable piece of test equipment 120, such as a digital ohm meter.

As further shown in FIG. 1, the conductive strips 102, 104 pass through the non-conductive layer 106 to an inner side of the non-conductive layer 106 (indicated by dashed lines) prior to passing around a proximal end 113 of the substrate 110. On the proximal end 113, first and second auxiliary contact members 115, 116 are disposed on the non-conductive layer 106. Each of the first and second auxiliary contact members 115, 116 is electrically coupled to a corresponding one of the first and second conductive strips 102, 104, respectively, by a plated-through hole 117.

In operation, the test device 100 may be used by pressing the first and second conductive strips 102, 104 into engagement with a conductive layer 122 (not shown) to be tested. The test equipment 120 then measures the electrical resistance $R_T$ of the conductive layer 122 between the first and second conductive strips 102, 104 in ohms per square. Because the first and second conductive strips 102, 104 are disposed on the compliant layer 111, the non-conductive layer 106 and conductive strips 102, 104 may flex to conform to the curvature of the conductive layer 122. In an alternate mode of operation, the first and second auxiliary contact members 115, 116 may be pressed into engagement with the conductive layer 122 under test, and the resistance $R_T$ of the conductive layer 122 is then determined by the test equipment 120. Due to their relatively smaller size, the auxiliary contact members 115, 116 may be used on smaller surfaces in comparison with the first and second conductive strips 106, 107.

Although desirable results have been achieved using the prior art test device 100, recent developments in conductive coatings are placing increased demands on such apparatus. For example, in the past, conductive coatings have been characterized by relatively high resistance per square values which were readily capable of accurate measurement using the prior art test device 100. More modern conductive coatings, however, have relatively smaller resistance per square, thereby posing a greater challenge to such test apparatus.

As the resistance of the conductive coating 122 decreases, the additional component of measured resistance attributable to the contact resistance between the surfaces of each conductive strip 102, 104 and the conductive coating 122 becomes an ever-increasing percentage of the resistance measured by the test equipment 120, thereby increasing the uncertainty associated with the measurement. In some cases, the resistance of the conductive coating 122 may even be smaller than the component of contact resistance between the conductive strips 102, 104 and the conductive coating 122, thereby preventing accurate measurement of the resistance of the conductive coating 122 using the prior art test device 100. Therefore, there is an unmet need in the art for an improved test device capable of accurately measuring the resistance of modern, low resistance conductive coatings on non-conducting composite structures.

SUMMARY OF THE INVENTION

The present invention is directed to apparatus and methods for measuring the electrical resistance of electrically-conductive materials. Apparatus and methods in accordance with the present invention may advantageously provide improved accuracy of electrical resistance measurements, and may enable the accurate measurement of the resistance of certain conductive materials having relatively small resistance.

In one embodiment, an apparatus includes a substrate, and first, second, third, and fourth elongated conductive members. Each conductive member has a first portion at least partially disposed on the substrate and a second portion. Each of the first portions is spaced apart from one or more adjacent first portions of the other elongated conductive members, and is engageable with the electrically-conductive material along a contact length. The first end portions of the second and third conductive members being disposed between the first portions of the first and fourth conductive members and spaced apart by a lateral distance. The apparatus may further include a source operatively coupled to the second portions of the first and fourth conductive members, and a meter operatively coupled to the second portions of second and third conductive members. In operation, the electrical resistance of the electrically-conductive material is determinable from a known value applied by the source and an observed value measured by the meter.

BRIEF DESCRIPTION OF THE DRAWINGS

The preferred and alternative embodiments of the present invention are described in detail below with reference to the following drawings.

DETAILED DESCRIPTION OF THE INVENTION

The present invention relates to apparatus and methods for measuring the electrical resistance of materials, and more specifically, to measuring the resistance of electrically-conductive coatings on aircraft surfaces and the like. Many specific details of certain embodiments of the invention are set forth in the following description and in FIGS. 2–6 to provide a thorough understanding of such embodiments. One skilled in the art, however, will understand that the present invention may have additional embodiments, or that the present invention may be practiced without several of the details described in the following description.

Figure 1:
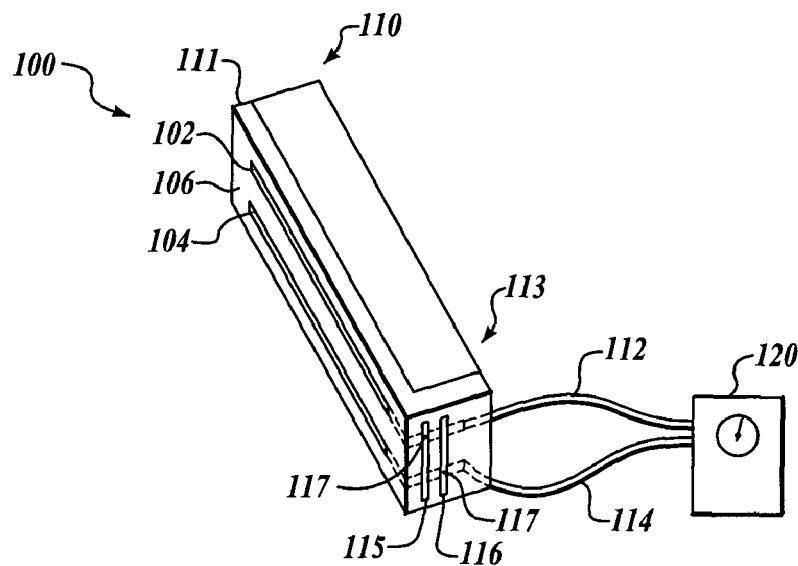
FIG. 1 is an isometric view of a test device for measuring electrical resistance of a conductive layer in accordance with the prior art.
Figure 2:
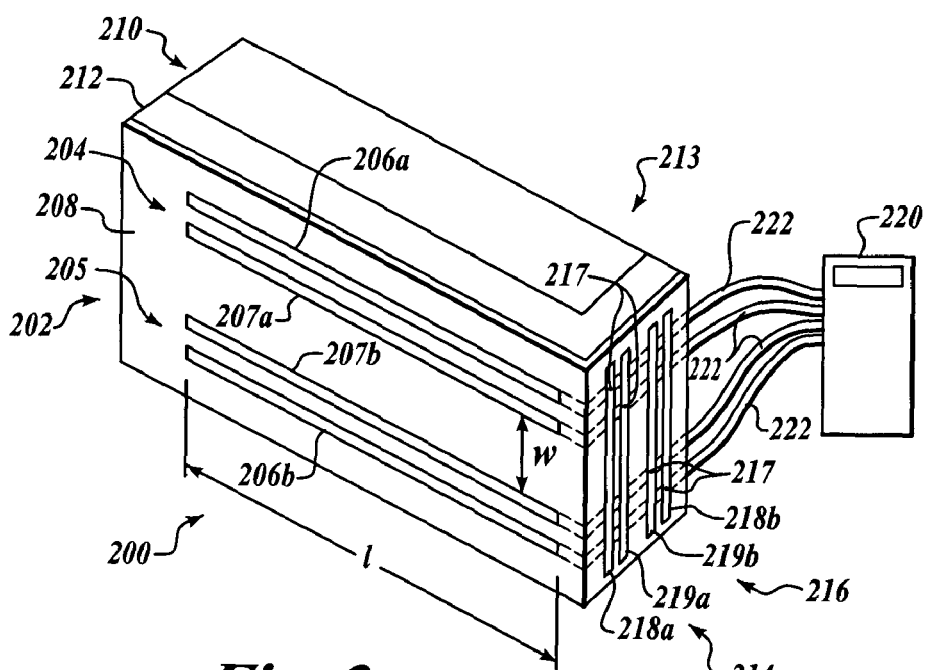
FIG. 2 is an isometric view of a test device for measuring electrical resistance of a conductive layer in accordance with an embodiment of the invention.
Figure 3:
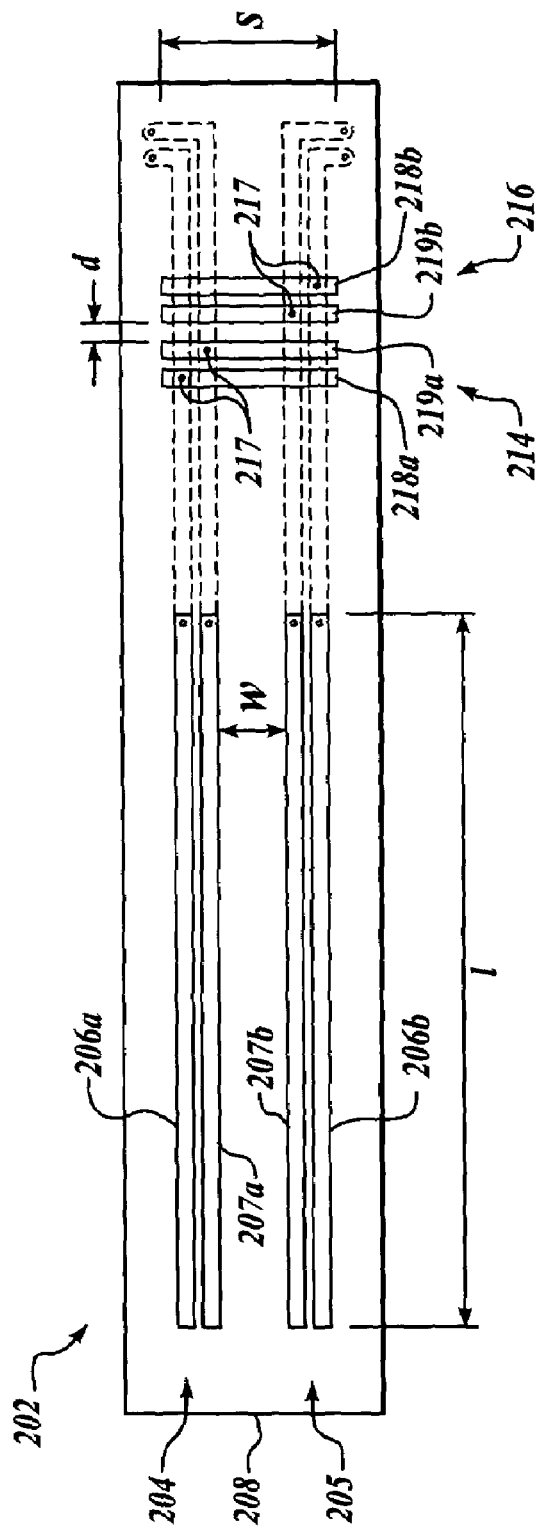
FIG. 3 is a top elevational view of a sensor portion of the test device of FIG. 2.

FIG. 2 is an isometric view of a test device 200 for measuring an electrical resistance $R_T$ of a conductive layer 122 in accordance with an embodiment of the invention. In this embodiment, the test device 200 includes a sensor portion 202 coupled to a substrate portion 210. FIG. 3 is a top elevational view of the sensor portion 202 of the test device 200 of FIG. 2. The sensor portion 202 includes first and second pairs 204, 205 of conductive contacts. Each pair 204, 205 includes an outer conductive contact 206 and an inner conductive contact 207. The outer and inner conductive contacts 206, 207 are disposed on a non-conductive layer 208 that is, in turn, attached to the substrate portion 210. In this embodiment, the substrate portion 210 includes a flexible, compliant layer 212 proximate the non-conductive layer 208 of the sensor portion 202. The conductive contacts 206, 207 may be formed of any desired conductive material, including copper, gold, aluminum or other suitable conductive material.

As further shown in FIGS. 2 and 3, the conductive contacts 206, 207 pass through the non-conductive layer 208 to an inner side of the conductive layer 206 (indicated by dashed lines) prior to passing around a proximal end 213 of the substrate 210. On the proximal end 213, first and second pairs of auxiliary contacts 214, 216 are disposed on the non-conductive layer 208. Each pair of auxiliary contacts 214, 216 includes an outer auxiliary contact 218 and an inner auxiliary contact 219 that are coupled to corresponding outer and inner conductive contacts 206, 207, respectively, by plated-through holes 217.

An article of test equipment 220 is coupled to the conductive contacts 206, 207 by a plurality of conductive leads 222. The test equipment 220 may be any of a variety of widely-known, commercially-available devices used for measuring electrical resistance, including, for example, digital ohm meters offered by Keithley Instruments, Inc. of Cleveland, Ohio, or by AVO Biddle Instruments Corporation of Blue Bell, Pa.

Figure 4:
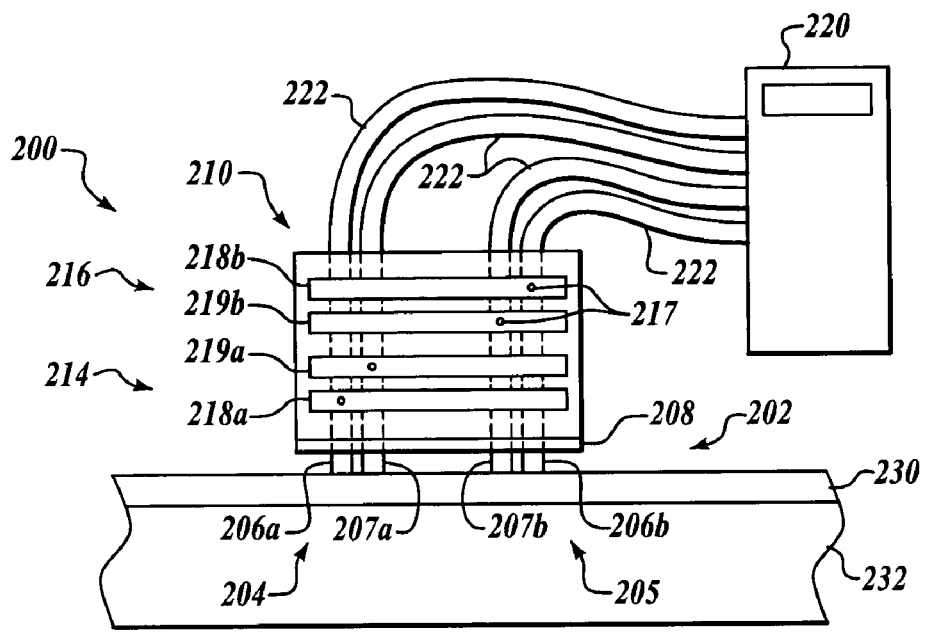
FIG. 4 is an enlarged end elevational view of the test device of FIG. 2 engaged with a conductive layer during a test in accordance with an embodiment of the invention.

FIG. 4 is an enlarged end elevational view of the test device 200 of FIG. 2 engaged with a conductive layer 230 during a test in accordance with a first mode of operation. The conductive layer 230 is formed on a non-conducting composite material 232. In this mode of operation, the test device 200 is used by pressing the first and second pairs of conductive contacts 204, 205 into engagement with the conductive layer 230 being tested. As described more fully below, the test equipment 220 then measures the electrical resistance $R_T$ of the conductive layer 230 between the inner conductive contacts 207 in ohms per square. Preferably, the non-conducting layer 208 and the conductive contacts 206, 207 of the sensor portion 202 are flexible so that, when the sensor portion 202 is disposed on the compliant portion 212 of the substrate 201 (FIG. 2), the sensor portion 202 may flex to conform to the curvature of the conductive layer 230.

In an alternate mode of operation (not shown), the test device 200 is re-positioned so that the first and second pairs 214, 216 of auxiliary contacts 218, 219 are engaged against the conductive layer 230 being tested. In this mode, the resistance $R_T$ of the conductive layer 230 between the inner auxiliary contacts 219 is measured by the test equipment 220.

Figure 5:
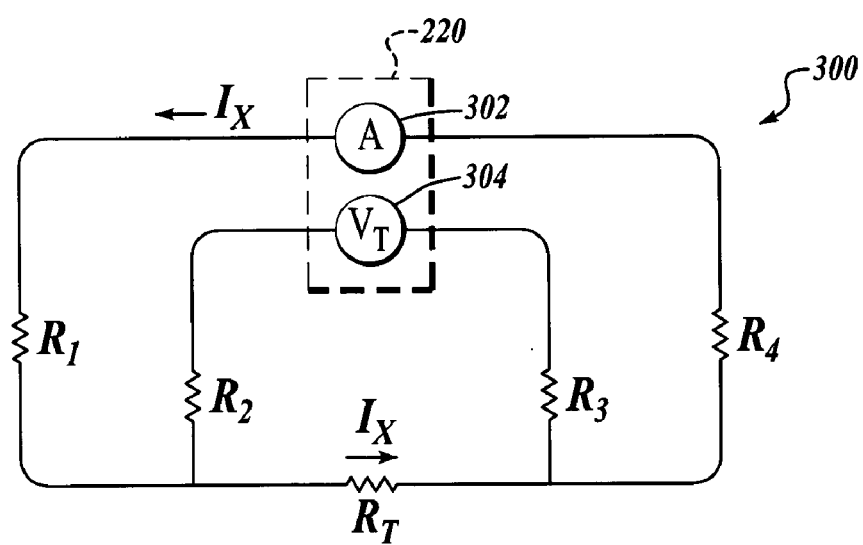
FIG. 5 is a circuit diagram for the device of FIG. 2 engaged with a conductive layer during a test in accordance with an embodiment of the invention.

FIG. 5 is a circuit diagram 300 for the test device 200 of FIG. 2 engaged with the conductive layer 230 during a test in accordance with an embodiment of the invention. In this embodiment, the resistance of the outer conductive contact 206a of the first pair 204 is represented by a first resistance $R_1$, the resistance of the inner conductive contact 207a of the first pair 204 is represented by a second resistance $R_2$, the resistance of the inner conductive contact 207b of the second pair 205 is represented by a third resistance $R_3$, and the resistance of the outer conductive contact 207b of the second pair 205 is represented by a fourth resistance $R_4$. Similarly, as set forth above, the electrical resistance of the conductive layer 230 between the inner conductive contacts 207 is represented by a test resistance $R_T$. A current source 302 is coupled in series between the first and fourth resistances $R_1$, $R_4$, and a meter 304 (e.g. a voltmeter) is coupled in series between the second and third resistances $R_2$, $R_3$. In addition, an ammeter that measures the known current $I_K$ (not shown in FIG. 5) may also be coupled in series between the first and fourth resistances $R_1$, $R_4$, either separately or included with the current source 302. The source 302 and the meter 304 may be included in the test equipment 220, or alternately, may be separate components. The circuit diagram 300 shown in FIG. 5 may be of a variety known as a Kelvin double bridge circuit, or may be any other suitable circuit.

In operation, the source 302 applies a known current $I_K$ to the circuit 300 which flows through the first resistance $R_1$, the test resistance $R_T$, and the fourth resistance $R_4$. The meter 304 measures a characteristic value, such as a test voltage $V_T$, across the test resistance $R_T$. Because only a negligible amount of current passes through the meter 304, practically no current passes through the second and third resistances $R_2$, $R_3$, and therefore, the current passing through the test resistance $R_T$ is approximately the known current $I_K$. Using the measured test voltage $V_T$ and the known current $I_K$, the test resistance $R_T$ is determinable using Ohm's law according to the following Equation 1:

$$R_T = V_T/I_K \tag{1}$$

Similarly, when the test device 200 is used in the alternate mode of operation with the first and second pairs of auxiliary contacts 214, 216 engaged with the conductive layer 230, the resistance of the conductive layer 230 is determined in the manner described above. With continued reference to the circuit diagram 300 shown in FIG. 5, in the alternate mode of operation, the resistance of the outer auxiliary contact 218a of the first pair 214 is represented by the first resistance $R_1$, the resistance of the inner auxiliary contact 219a of the first pair 214 is represented by the second resistance $R_2$, the resistance of the inner auxiliary contact 219b of the second pair 216 is represented by the third resistance $R_3$, and the resistance of the outer auxiliary contact 218b of the second pair 216 is represented by the fourth resistance $R_4$. Thus, by applying the known current $I_K$ across the outer auxiliary contacts 218, the test resistance $R_T$ of the conductive layer 230 may be determined by measuring the test voltage $V_T$ between the inner auxiliary contacts 219.

Referring to FIGS. 2 and 3, if the lateral distance w between the inner conductive contacts 207 is equal to the contact length l such that the area of the conductive layer 230 under test that lies between the inner conductive contacts 207 is a square, then the measured value of the test resistance $R_T$ is the equal to the resistance of the conductive layer 230 in ohms per square. This is the true regardless of the actual physical dimension of the lateral distance w and the contact length l so long as these values are equal.

On the other hand, if the lateral distance w is not equal to the contact length l, such that the test area of the conductive layer 230 that lies between the inner conductive contacts 207 is not square (e.g. rectangular), then a scaling factor is applied to the test resistance $R_T$ in order to compute the resistance of the conductive layer 230 in the standard unit of measurement, namely, ohms per square. For example, as shown in FIG. 3, if the lateral distance w is one-tenth of the contact length l, then the test resistance $R_T$ is multiplied by a scaling factor of 10 in order to compute the resistance of the conductive layer 230 in ohms per square.

It may be noted that during testing, current losses may occur within the conductive layer 230 outwardly from the ends of the test area that are not bounded by the conductive contacts 206, 207. These losses may contribute to any uncertainty that may be associated with the measurement of the test resistance $R_T$. Therefore, it may be desirable to design the test device 200 such that the lateral distance w is relatively small in comparison to the length l in order to reduce errors due to current losses.

For example, a 1 mm lateral distance of a 1 mm by 1 mm probe may have the same current losses as a 2 ft by 2 ft probe. Similarly, a 1 mm by 10 mm probe may have the same current losses as the 1 mm by 1 mm probe because the lateral distance w is the same width and the current is allowed to flow around two ends, but the error due to the current losses gets divided by 10 when the correction is applied. In a particular aspect of the invention, the geometric correction for a probe with parallel and equal length conductive members is the lateral distance w divided by the contact length l (i.e. w/l).

Preferably, the outer and inner conductive contacts 206, 207 of each pair 204, 205 may be substantially parallel. Similarly, the first and second pairs 204, 205 may also be substantially parallel with each other. Such parallelism of the conductive contacts 206, 207 may simplify the process of data reduction and may improve measurement accuracy. If the conductive contacts 206, 207 are non-parallel, however, the non-parallelism may be measured and accounted for in the data reduction algorithm. Furthermore, the contact lengths l of all of the conductive contacts 206, 207 may be equal, as shown in FIGS. 2 and 3, or alternately, may be unequal. Embodiments having unequal contact lengths l of the conductive contacts 206, 207 may include additional correction factors within the data reduction algorithm, as may be determined by persons of ordinary skill in the art.

The test device 200 advantageously provides improved measurement of the electrical resistance of the conductive layer 230. Because the test resistance $R_T$ is measured between the inner conductive contacts 207, and because approximately no current (or only a negligible amount of current) passes through the inner conductive contacts 207, the additional component of measurement uncertainty caused by the resistance associated with the surface-to-surface contact between the conductive contacts and the conductive layer 230 is eliminated from the resulting measurement. The test device 200 may therefore be employed to measure the resistance of conductive coatings having relatively small resistance, including such coatings having a resistance value smaller than the surface-to-surface contact resistance between the conductive contacts and the conductive coating.

Figure 6:
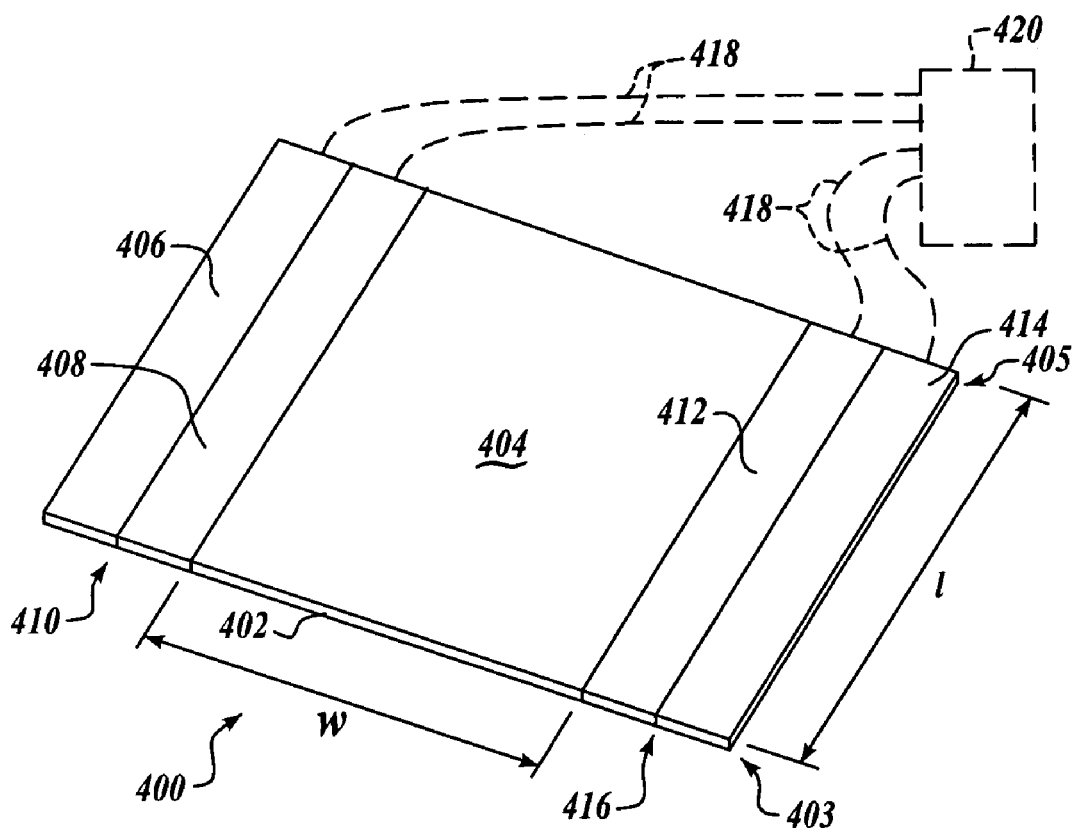
FIG. 6 is an elevational view of an apparatus for measuring electrical resistance of a conductive layer in accordance with an alternate embodiment of the invention.

FIG. 6 is an elevational view of an apparatus 400 in accordance with an alternate embodiment of the invention. In this embodiment, the apparatus 400 includes a non-conductive substrate 402 having a conductive material 404 disposed thereon. First and second conductive members 406, 408 are disposed on the conductive material 404 and are separated by a first gap 410. Similarly, third and fourth conductive members 412, 414 are disposed on the conductive material 404 and are separated by a second gap 416. In the embodiment shown in FIG. 6, the conductive members 406, 408, 412, 414 are wrapped over the leading and trailing edges 403, 405 of the conductive layer 404 and the non-conductive substrate 402.

In a particular aspect, the first and second conductive members 406, 408 are formed by attaching a strip of conductive tape or other suitable conductive material to the conductive coating 404, and then cutting the strip of conductive tape to form the first gap 410. The third and fourth conductive members 412, 414 and the second gap 416 may be formed in a similar fashion. Alternately, the conductive members 406, 408, 412, 414 may simply be formed using strips of conductive tape (e.g. copper tape) having a layer of conductive adhesive that attaches the conductive tape to the conductive layer 404.

As further shown in FIG. 6, the second and third conductive members 408, 412 are separated by a lateral distance w, and all of the conductive members 406, 408, 412, 414 contact the conductive material 404 along a contact length l. In this embodiment, the lateral distance w is equal to the contact length l. The apparatus 400 may further include a plurality of conductive leads 418 that couple each of the conductive members 406, 408, 412, 414 to an article of test equipment 420. As described above, the test equipment 420 may be any acceptable, commercially-available device that includes the components necessary for conducting tests and performing measurements of the resistance of the conductive material 404.

In operation, the test equipment 420 applies a known current $I_K$ (approximately) into the first conductive member 406, across the conductive material 404, and out through the fourth conductive member 414, and measures the resulting test voltage $V_T$ existing between the second and third conductive members 408, 412. In the manner described above, the test resistance $R_T$ of the conductive material 404 is determined from the test voltage $V_T$ and the known current $I_K$. Because the lateral distance w is equal to the contact length l, the area between the second and third conductive members 408, 412 is a square and the measured test resistance $R_T$ of the conductive material 404 is measured in the standard unit, ohms per square. In other words, no scaling factor is necessary, and the measurement is the same whether the square is, for example, 1 cm by 1 cm or 3.5 inch by 3.5 inch.

The apparatus 400 advantageously provides improved measurement of the electrical resistance of the conductive material 404. As described above, because the test resistance $R_T$ is measured between the second and third conductive members 408, 412, and because approximately no current (or only a negligible amount of current) passes through these conductive members 408, 412, the measurement uncertainty caused by the surface-to-surface contact resistance between the conductive members 406, 408, 412, 414 and the conductive material 404 is eliminated from the resulting measurement. The apparatus 400 may therefore provide improved measurement accuracy, especially for conductive materials having relatively small electrical resistance. Also, because the conductive material 404 is co-extensive with the contact length l of the conductive members 406, 408, 412, 414, there are no current losses due to the bounded ends of the test area, thereby reducing or eliminating another component of measurement uncertainty.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

What is claimed is:

1. An apparatus for measuring an electrical resistance of an electrically-conductive material, the apparatus comprising:
   a substrate having a first side and an adjacent second side that is perpendicular to the first side; and
   first, second, third, and fourth elongated conductive members, each conductive member having a first portion at least partially disposed on the first side of the substrate and a second portion extending along the second side, each of the first portions being spaced apart from one or more adjacent first portions and the second portions being coupled to auxiliary contacts disposed on the second side, the first portion and the auxiliary contacts being selectively engageable with the electrically-conductive material along respective contact lengths, the first end portions of the second and third conductive members being disposed between the first portions of the first and fourth conductive members and spaced apart by a lateral distance.

2. The apparatus of claim 1, further comprising:
   a source operatively coupled to the second portions of the first and fourth conductive members; and
   a meter operatively coupled to the second portions of second and third conductive members.

3. The apparatus of claim 2, wherein the source includes a current source.

4. The apparatus of claim 2, wherein the meter includes a voltage meter.

5. The apparatus of claim 1, wherein at least two of the first portions are substantially parallel.

6. The apparatus of claim 1, wherein at least two of the contact lengths are equal.

7. The apparatus of claim 1, wherein the contact lengths are substantially equal to the lateral distance.

8. The apparatus of claim 1, wherein the contact lengths are substantially longer than the lateral distance.

9. The apparatus of claim 1, wherein the first portions of the first and second conductive members are spaced apart by a first gap and the first portions of the third and fourth conductive members are spaced apart by a second gap, the first and second gaps being smaller than the lateral distance.

10. The apparatus of claim 1, wherein the substrate includes a compliant substrate and the first portions comprise flexible portions.

11. An apparatus for measuring a resistance of a conductive layer, the apparatus comprising:
    a non-conductive substrate having a first side and an adjacent second side; that is perpendicular to the first side
    first and second pairs of conductive leads, each pair of conductive leads including an outer lead and an inner lead, each conductive lead having a first portion disposed on the first side and a second portion disposed on the second side, the second portion being coupled to auxiliary contacts disposed on the second side, the first portion and the auxiliary contacts extending along respective contact lengths and being selectively engageable with the conductive layer, the first portions of the inner leads being spaced apart by a lateral distance, the first portions of the outer leads being positioned on opposing sides of the first portions of the inner leads; and
    a device operatively coupled to the second portions of the conductive leads, the device being operable to apply a known applied current to the outer leads, and to determine a resulting voltage between the inner leads.

12. The apparatus of claim 11, wherein at least two of the first portions are substantially parallel.

13. The apparatus of claim 11, wherein at least two of the contact lengths are equalized.

14. The apparatus of claim 11, wherein at least two of the contact lengths are equalized to the lateral distance.

15. The apparatus of claim 11, wherein the lateral distance is substantially less than the contact lengths.

16. The apparatus of claim 11, wherein the device includes a Kelvin double bridge circuit.

17. The apparatus of claim 11, wherein the substrate includes a compliant substrate and the first portions comprise flexible portions.

18. A method of measuring a resistance of a conductive layer, the method comprising:
    providing first and second pairs of conductive leads, each conductive lead having a first portion disposed on a first face of a supporting substrate and a second portion disposed on an adjacent second face of the substrate that is perpendicular to the first face, the second portion being coupled to auxiliary contacts disposed on the second face, each pair of conductive leads including an outer lead and an inner lead, the first portions of the inner leads being adjacent and spaced apart by a lateral distance, the first portions of the outer leads being positioned on opposing sides of the first portions of the inner leads;
    selectively engaging one of the first portions of the first and second pairs of conductive leads and the auxiliary contacts with the conductive layer along a respective contact lengths;
    applying an electrical current to the second portions of the outer leads; and
    determining a resulting voltage between the inner leads.

19. The method of claim 18, each first portion is approximately parallel with one or more adjacent first portions.

20. The method of claim 18, wherein engaging the first portions of the first and second pairs of conductive leads with the conductive layer includes engaging the first portions of the first and second pairs of conductive leads with the conductive layer along a contact length approximately equal to the lateral distance.

21. The method of claim 18, wherein engaging the first portions of the first and second pairs of conductive leads with the conductive layer includes engaging the first portions of the first and second pairs of conductive leads with the conductive layer along a contact length substantially greater than the lateral distance.

22. The method of claim 18, further comprising computing resistance based on the applied electrical current and the resultant voltage.

23. The method of claim 18, wherein computing the resistance includes applying a scaling factor based on a non-equality of the lateral distance and the contact length.

24. The method of claim 18, wherein computing the resistance includes applying a scaling factor based on a non-parallelism of the first portions of the conductive leads.

* * * * *